United States Patent
Ahlbäumer

(10) Patent No.: US 8,584,376 B2
(45) Date of Patent: Nov. 19, 2013

(54) INSOLE WITH REINFORCEMENT ELEMENT

(75) Inventor: Georg Ahlbäumer, St. Moritz (CH)

(73) Assignee: Cetec AG (LI)

( * ) Notice: Subject to any disclaimer, the term of this patent is extended or adjusted under 35 U.S.C. 154(b) by 804 days.

(21) Appl. No.: 12/733,632

(22) PCT Filed: May 30, 2008

(86) PCT No.: PCT/EP2008/004325
§ 371 (c)(1),
(2), (4) Date: Jul. 2, 2010

(87) PCT Pub. No.: WO2009/039902
PCT Pub. Date: Apr. 2, 2009

(65) Prior Publication Data
US 2010/0275469 A1 Nov. 4, 2010

(30) Foreign Application Priority Data

Sep. 19, 2007 (DE) .................... 20 2007 013 120 U

(51) Int. Cl.
*A43B 13/38* (2006.01)
*A43B 7/06* (2006.01)
*A43B 7/22* (2006.01)
*A43B 23/22* (2006.01)

(52) U.S. Cl.
USPC .......... 36/3 B; 36/91; 36/43; 36/76 C; 36/147

(58) Field of Classification Search
USPC ....... 36/3 B, 91, 43, 76 C, 147, 107, 148, 151
See application file for complete search history.

(56) References Cited

U.S. PATENT DOCUMENTS

| 5,404,659 | A | 4/1995 | Burke | |
|---|---|---|---|---|
| 6,301,807 | B1 | 10/2001 | Gardiner | |
| 6,502,330 | B1 * | 1/2003 | David et al. | 36/88 |
| 6,732,457 | B2 * | 5/2004 | Gardiner | 36/155 |
| 7,617,618 | B2 * | 11/2009 | Ahlbaumer | 36/3 B |
| 7,707,751 | B2 * | 5/2010 | Avent et al. | 36/150 |
| 7,958,653 | B2 * | 6/2011 | Howlett et al. | 36/44 |
| 2009/0165334 | A1 * | 7/2009 | Kantro et al. | 36/91 |

FOREIGN PATENT DOCUMENTS

| DE | 20314288 | 11/2003 |
|---|---|---|
| WO | WO 2004 023916 | 3/2004 |

OTHER PUBLICATIONS

International Searching Authority, English translation of a Written Opinion dated Sep. 29, 2008.

* cited by examiner

*Primary Examiner* — Ted Kavanaugh
(74) *Attorney, Agent, or Firm* — Lowe Graham Jones PLLC

(57) ABSTRACT

An insole which is substantially adapted to the profile of a human foot and comprises, in the mid-foot region, an elastically deformable arch facing the foot, characterized in that a reinforcement element is located on the side of the insole facing away from the foot in the region of the arch, said reinforcement element being made of a different material with a greater stiffness than the material of the insole and having a convex shape.

13 Claims, 1 Drawing Sheet

INSOLE WITH REINFORCEMENT ELEMENT

CROSS REFERENCE TO RELATED APPLICATIONS

This United States Utility Patent Application represents the national phase of International Application PCT/EP2008/004325 titled "INSOLE WITH REINFORCEMENT ELEMENT" filed on May 8, 2008 and claiming priority from prior filed, German National Application Serial No. 20 2007 013 120.8 filed on Sep. 19, 2007.

TECHNICAL FIELD

This invention relates to an insole which is essentially adapted to the profile of a human foot and has, in the mid-foot region, an elastically deformable dome-like arch that faces the foot.

BACKGROUND OF THE INVENTION

Insoles, in particular insertable insoles, for shoes have numerous functions. They improve the wearing comfort of shoes, e.g. by padding out the places facing the sole of the foot or by the provision of damping elements. They are also used in the medical sector to correct faults in the gait of a person or to relax or stabilize the foot.

There are also insoles that vent the interior of the shoe to counter unpleasant odors developing in the interior of the shoe. In particular with sports persons and people with heavy sweat formation, human exudation in the interior of the shoe leads to a possible strong odor which can be largely compensated by appropriately venting the interior of the shoe.

Due to the described general problems, numerous patent documents deal with the formation of special shoe insoles which increase the wearing comfort of shoes or serve medical purposes.

For example, in patent specifications U.S. Pat. No. 5,404,659 and U.S. Pat. No. 6,301,807 insoles are described which, due to a filled out insole arch or an insole arch provided with supporting elements, cause a proprioceptive effect on the wearer of a shoe with such an insole, thereby reinforcing a foot in its structure, whereby, for example, the risk of injury is reduced.

Numerous patent specifications and applications deal with the ventilation of the interior of the shoe. For example, applications JP-11032809A and JP-2000106908A show the inner ventilation of shoes, whereby the ventilation in both cases is provided by a pump integrated into the insole. In the application document JP-2000106908A the ventilation system also exhibits a duct, connected to the pump, and having ventilation ports, through which the air in the pump is pumped upon compression thereof into the interior space of the shoe. Furthermore, there are also cypress chips in the pump which are intended to aromatize the ventilating air.

FR-A-2 395 719 discloses an insole which is substantially adapted to the profile of a human foot and has, in the mid-foot region, an elastically deformable dome-like arch that faces the foot and includes a venting port.

EP-0 903 984-B1 shows a configuration of a shoe internal ventilation system, consisting of a shoe outsole, an insole and a corresponding midsole. In this respect the invention exhibits air chambers between midsole and shoe outsole in the front section of the foot, the air from the chambers being passed into the shoe interior through holes in the insole in the front foot section during movement due to deformation in said sections.

EP-1 536 710-A1 shows an insertable insole made of an elastic plastic material with elastically deformable arch with punched-in venting ports and radially running grooves on the underside, through which the air ventilated out of the interior of the shoe is exchanged with outside air.

Since a shoe insole is a mass-produced article, it is especially important to keep the technical effort and the financial manufacturing costs of such an article as low as possible. At the same time the article should be of a constant high quality.

BRIEF SUMMARY OF THE INVENTION

To achieve these objectives, it is the object of the present invention to improve the insole known from EP-1 536 710-A1 such that a product with a long service life is created that shows a constant wearing quality throughout its life and, in combination with an appropriate shoe, improves the wearing comfort in that it inter alia aerates and de-aerates, respectively, the interior of the shoe.

These objects are solved in an inventive way by the subject matter of claim 1. Advantageous embodiments of the invention are the subject matter of several subclaims.

The present invention is based on the knowledge that due to the formation of an elastically deformable dome-like arch that faces the foot the wearing comfort of a shoe can be substantially improved with the insole according to the invention. Due to the formation of an arch on the upper side of the insole, the insole lies in contact with the sole of the foot throughout the complete movement sequence during walking. This increases subjectively the wearing comfort for the wearer of a shoe with the insole according to the invention. If the arch of the insole is in the mid-foot region, then the forces acting during the movement can be used especially advantageously for the deformation of the arch and consequently for the air circulation (ventilation) in the shoe.

To ensure that the desired wearing comfort lasts for a long time, it is provided according to the invention that the insole is equipped with an insertable part for reinforcing purposes that is either loosely inserted or firmly connected to the insole.

The shape of the insertable part is preferably adapted to the arch of the insole. The base area of the arch describes an ellipse, but it has been turned out to be particularly advantageous for a more uniform force distribution when the base area of the reinforcement element is configured in the shape of a bone.

The bone shape of the insertable part can be given an asymmetrical form, so that e.g. the bone side facing the tip of the foot is enlarged or the side facing the foot end is reduced in size so as to take into account the anatomical features of the foot and of the insole adapted thereto in its shape.

To promote the resilient properties of the insertable part, it has turned out to be advantageous when the plastic material used therefor has a higher stiffness than the plastic material used in the insole. In addition, the resilient properties of the bone-shaped insertable part can be improved by a later formation or a previous recessing of slits.

Due to the deformation of the unfilled insole arch formed in the mid-foot region, which is caused by walking, air is pumped through venting ports into the interior of the shoe. It is here irrelevant whether the reinforcement element is connected to the insole either directly by form locking or with the help of a suitable adhesive by material locking without the formation of cavities.

It is particularly expedient when the air is simultaneously discharged via venting grooves extending on the underside of the insole so as to permit an air exchange in the interior of the shoe.

Furthermore, it is advantageous for an efficient air exchange when the grooves on the underside of the insole extend radially from the arch to the outer edges of the insole.

As the arch resumes its shape after having been stressed, the air is sucked through the venting holes out of the shoe interior into the air chamber formed by the region positioned between arch and shoe insole, and fresh air from the outside is simultaneously passed through the venting grooves into the air chamber. This permits a constant air exchange in the shoe interior. The venting holes are expediently formed by perforation of the shoe insole, but attention should be paid that especially the venting holes positioned in the region of the arch are not covered by the insertable part positioned thereunder. This can be accomplished in that the position of the venting holes is matched with the recesses in the insertable part. Optionally, further venting holes are formed in the region of the forefoot, with the holes matching the grooves provided on the underside of the shoe insole.

As described, the wearing comfort can be increased due to the formation of an arch on the insole and at the same time a simple ventilation of the shoe interior can be achieved without large material and financial expenses.

Due to the properties advantageous for an insole, such as flexibility, stress capability, etc., it is reasonable to form the insole from an elastic plastic material or from another material which has the said properties.

It is particularly of advantage when the insole is an insertable insole because said insole can be exchanged, if necessary, in case of damage or strong wear.

The wearing comfort can be increased still further by a textile on the upper side of the insole facing the foot.

The insole according to the invention can be used especially effectively in an appropriately adapted shoe. In this respect it is reasonable that the shoe facilitates in a supporting way the circulation of the air in the shoe interior, i.e. the supply and discharge of air, via the venting grooves in the insole.

The use of a gas-permeable membrane, at least at the points of the venting grooves ending at the shoe, which enables an exchange of air in the shoe interior via the venting grooves, has proved to be particularly advantageous in this connection.

The membrane is intended to prevent the penetration of fluids and dirt into the shoe interior and to permit the flow of the fluid from the shoe interior to the outside. For example, materials similar to GORE-TEX can be considered for the membrane. The membrane is advantageously integrated into the outer material of the shoe.

BRIEF DESCRIPTION OF THE DRAWINGS

The invention shall now be explained in more detail based on the preferred embodiments illustrated in the enclosed drawings. Similar or corresponding details are given the same reference numerals in the figures. The following is shown in.

DETAILED DESCRIPTION OF THE INVENTION

Figure 1:
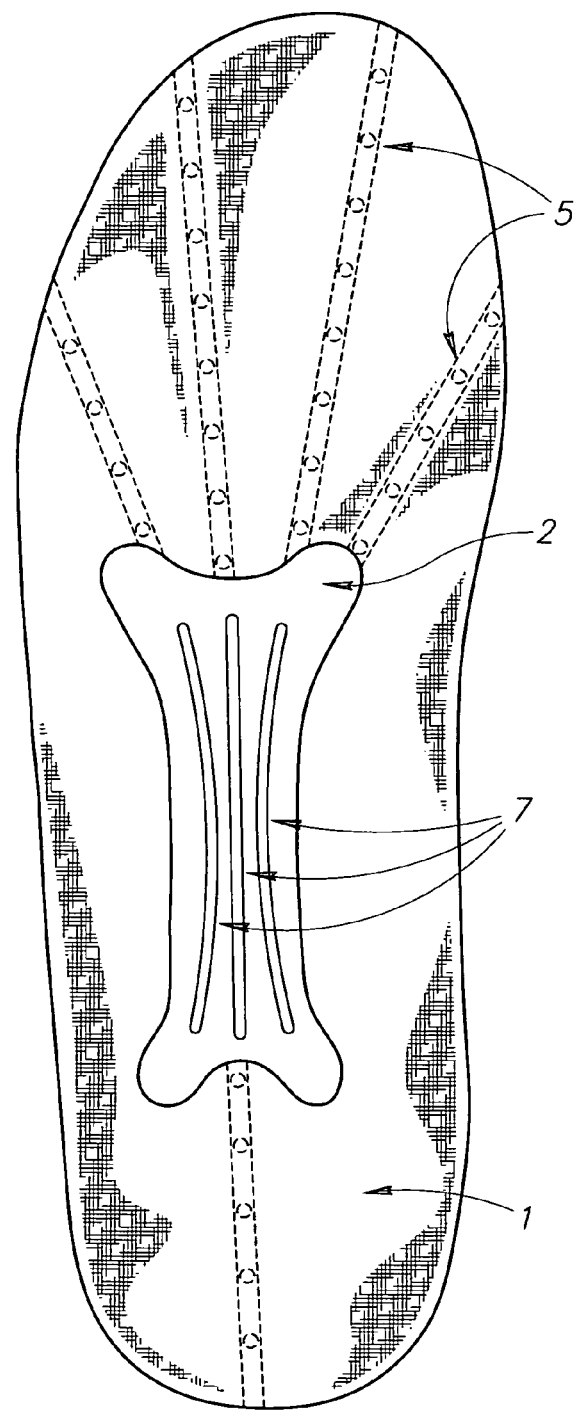
FIG. 1 the upper side of an insole according to the invention facing the foot.
Figure 2:
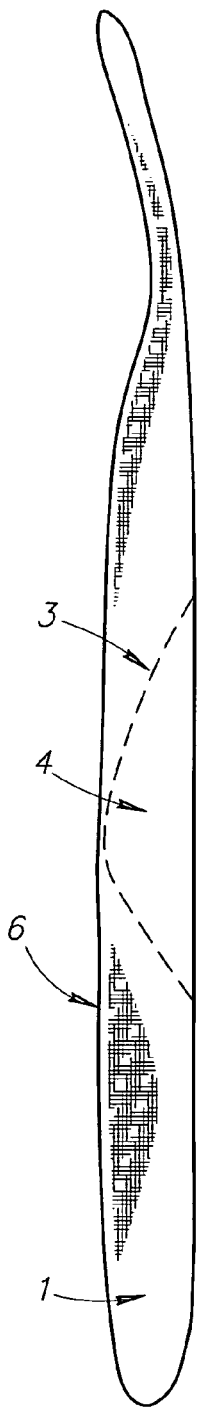
FIG. 2 a side view of the insole from sketch 1.

FIG. 1 shows as an example a view on the upper side of an insole 1 according to the invention which is facing the foot and of the bone-shaped insertable part 2 fitted thereinto. The shape of the shoe sole is here adapted essentially to the profile of a human foot. As can be seen from the side view of FIG. 2, the insole 1 has an arch 3 in its center.

The arch 3 has formed thereon a plurality of radially running venting grooves 5. The venting grooves run along the underside of the insole 1 on the outer edge of the insole 1. Furthermore, an edge prominence 6 is provided on the outside of the insole 1, said edge prominence essentially extending between the ball region and the heel region. The edge prominence simplifies the insertion of the insole 1 into a shoe if it is formed as an insertable insole, and increases the wearing comfort.

In addition, a thin layer formed by a textile is provided on the upper side of the insole 1.

The arch 3 facing the foot forms an air chamber on the underside, facing the shoe. The air from the shoe interior can be exchanged with air from outside the shoe via grooves 5. This provides ventilation of the shoe interior.

In this respect it is expedient if the grooves 5 are not so deformable due to the stress from the human foot during walking that no exchange of air can take place. A certain stiffness of the grooves 5 is therefore to be provided. Furthermore, sketch 1 shows a reinforcement element 2 which due to its convex shape matches the arch of the insole 1, so that both parts can either simply be placed one on top of the other, resulting in form locking, or the two parts are glued to each other, resulting in material locking.

If pressure is exerted by the foot on the insole during walking, the cavity 4 of the arch 3 is thereby reduced in size. While in EP-1 536 710-A1 the return movement into the initial position of the arch is exclusively achieved through the elasticity of the insole, the reinforcement element 2 underlying this application actively supports the restoring movement in that it is made from an elastic material exhibiting a resilient property.

The reinforcement element is provided with longitudinal slits, so that the resilient material properties are advantageously supported in that upon compression the webs formed between the slits can store additional translation energy, which are again released during the restoring movement, so that the restoring movement is always faster in a variant without a reinforcement element.

Since the reinforcement element is used on the side of the insole facing away from the foot, it can be made from a stable plastic material without impairment of the wearing comfort of the shoe with insole.

Hence, the reinforcement element increases the service life of the insole, which would wear at an accelerated pace on account of its own resilient property without said reinforcement element.

The invention claimed is:

1. An insole (1) which is substantially adapted to the profile of a human foot and comprises, in a mid-foot region, an elastically deformable arch (4) facing the foot,
    wherein
        a reinforcement element (2) is located on a side of the insole facing away from the foot in the region of the arch, said reinforcement element being made of a different material with a greater stiffness than the material of the insole and having a convex shape and wherein the reinforcement element has a shape resembling a bone, narrower in the middle with two enlarged ends, and comprises longitudinal slits (7) closed at a forward and a rear end, of which a central slit extends in straight fashion and outer slits extend slightly bent to the outside in conformity with the bone shape of the reinforcement element.

2. A shoe with insole according to claim 1.

3. The insole according to claim 1, characterized in that the reinforcement element and the insole (1) are integrally formed such that the convexity of the reinforcement element (2) matches the arch of the insole.

4. The insole according to claim 1, characterized in that the reinforcement element is adapted such that the insole (1) and the reinforcement element (2) are interconnectable either directly by form locking or with a suitable adhesive by material locking without the formation of cavities.

5. The insole according to claim 1, characterized in that the reinforcement element exhibits resilient properties due to a dome-like arch.

6. The insole according to claim 1, characterized in that the reinforcement element consists of a shaped plastic material.

7. The insole according to claim 6, characterized in that the insole in the region of the arch comprises small holes (3) for ventilation, said holes are not impeded by the reinforcement element and are provided to support air circulation.

8. The insole according to claim 7, characterized in that the insole is provided on its underside with grooves (5) through which air ventilated out of the shoe interior is replaced by outside air.

9. The insole according to claim 8, characterized in that venting grooves (5) extend substantially radially from the arch (4) to the outer edge of the insole.

10. The insole according to claim 9, characterized in that the insole is made from an elastic plastic material.

11. The insole according to claim 9, characterized in that the insole on its side facing the foot has a surface formed by a textile.

12. The insole according to claim 11, characterized in that the insole is an insertable insole.

13. The insole according to claim 9, characterized in that the textile is provided with a perforation by way of small holes, arranged such that said holes support ventilation.

* * * * *